United States Patent [19]

Zimmerman et al.

[11] Patent Number: 5,037,410
[45] Date of Patent: Aug. 6, 1991

[54] DISPOSABLE ARTICLES COMPRISING COMPOSTIBLE COMPONENTS

[76] Inventors: Robert R. Zimmerman, 10247 S. Crossett Hill Dr., Pickerington, Ohio 43147; Tamela A. Viers, 4257 Golden Gate Sq., Columbus, Ohio 43224

[21] Appl. No.: 564,084

[22] Filed: Aug. 8, 1990

[51] Int. Cl.$^5$ .............................................. A61F 13/15
[52] U.S. Cl. ....................................... 604/358; 604/373
[58] Field of Search .................... 604/358, 364, 373; 128/156

[56] References Cited

U.S. PATENT DOCUMENTS

| | | | |
|---|---|---|---|
| 4,430,086 | 2/1984 | Repke | 604/385.2 |
| 4,626,252 | 12/1986 | Nishizawa et al. | 607/373 |
| 4,944,734 | 7/1990 | Wallach | 604/358 |
| 4,964,857 | 10/1990 | Osborn | 604/358 |

*Primary Examiner*—Randall L. Green
*Assistant Examiner*—K. Reichle

[57] ABSTRACT

Disposable articles that mitigate environmental problems when charged into solid waste landfills have a moisture barrier layer in the form of a compostible flexible sheet composed of 20–80% by weight unvulcanized, uncured C4–C6 alkadiene elastomer, e.g., natural rubber, 5–20% of modifier, e.g., casein, dextrose, starch or mixtures thereof, 1–40% filler, e.g., titanium dioxide or fibrous clay, 0–30% wax, e.g., carnauba wax, 0–40% styrene resin, e.g., polystyrene, 0–10% additive, e.g., bis-steramide, and 0–20% yeast. Typically, the sheets have a thickness of about 1 to 10 mils and an ultimate tensile strength of at least 200 grams per inch of width.

12 Claims, No Drawings

DISPOSABLE ARTICLES COMPRISING COMPOSTIBLE COMPONENTS

BACKGROUND OF THE INVENTION

1. Field of the Invention

This application relates to disposable articles comprising compostible components. More particularly, it concerns disposable garments, e.g., diapers, disposable containers, e.g., bags, and other disposable articles comprising unique, compostible, moisture barrier sheets.

2. Description of the Prior Art

The disposal of solid waste has become a worldwide problem because of its magnitude with great economic and environmental ramifications. As a consequence, producers of disposable articles, e.g., diapers, containers, etc., are under increasing pressure to assist in providing a solution, particularly in providing articles that will be environmentally acceptable in solid waste landfills. Several approaches have been taken to address this concern. One has been to employ article construction materials that can be degraded by microorganisms or enzymes or other substances that they secret. This is particularly important if the disposable article will find its way into a compost facility.

There has been a concerted effort to educate the general public concerning the solid waste disposal problems and to get its cooperation in helping to mitigate same, e.g., to participate in removing recyclable items from trash. This has resulted in the general use of the term biodegradable to indicate that a material so classified is environmentally acceptable for disposal in solid waste landfills. However, this term appears to be too ambiguous for use by disposable article industries and government agencies so a more specific term has evolved, namely, compostible, which signifies that a material so classified is capable of controlled biological decomposition under predominantly aerobic conditions into material which can be easily and safely stored, handled and used without creating a threat to public health and/or the environment.

Although the environmental aspects of waste disposal have received great attention in recent years, waste disposal problems have concerned disposable article manufactures for many years resulting in many disclosures for article improvements seeking to assist in mitigation of the problems. For example, see U.S. Pat. Nos. 1,564,498; 1,979,899; 3,563,244; 3,616,797; 3,654,064 and 3,838,692.

The present invention further addresses the environmental problems of solid waste disposal of throw-away articles and provides improved articles of this type to assist in mitigation thereof.

OBJECTS

A principal object of the invention is the provision of disposable articles comprising unique compostible components.

A further object is the provision of disposable garments, e.g., diapers, disposable containers, e.g., bags, and other disposable articles comprising unique, compostible, moisture barrier sheets.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects are accomplished in accordance with the invention by the provision of disposable articles comprising as an independent component thereof a compostible flexible sheet composed of 20–80% by weight unvulcanized, uncured C4–C6 alkadiene elastomer, 5–20% of modifier selected from casein or equivalent animal or plant protein, dextrose, starch or mixtures thereof, 1–40% filler, 0–30% wax, 0–40% styrene resin, 0–10% additive and 0–20% yeast, all said percentages being by weight based on the total weight of said sheet. Within these limits, the proportions of ingredients in the sheets are selected so the sheet has an ultimate tensile strength of at least 200 grams per inch of width in thickness of about 1 to 10 mils and an elongation without breakage of at least 100%, particularly at least 400%. Typically, cast sheets used in fabrication of articles of the invention with a thickness of 1 to 2 mils have a tensile strength of at least 100 grams per inch of width at 100% elongation and an ultimate tensile strength of at least 400 grams per inch of width at an elongation of at least 400%.

By way of example, the new compostible sheets having appreciable moisture barrier properties used in accordance with the invention may consist essentially of 35–75% unvulcanized, uncured natural rubber, 10–15% casein, 10–20% wax and 1–35% inorganic filler.

In a preferred embodiment of the invention, the disposable article is a diaper, e.g. infant or adult, and the compostible sheet is the so-called backsheet (outer cover) of the diaper. As to methods of manufacture and construction of disposable diapers see U.S. Pat. Nos. 4,050,462 and 4,769,024 the disclosures of which are incorporated herein by reference.

In other embodiments, the disposable article is a surgical gown, bib, apron or bag, e.g., trash, garbage, tote or like bag.

Disposal articles incorporating compostible sheets as described above may be fabricated by any known production operation and equipment so such operations and methods form no essential part of the invention. Further, disposable diapers and other articles may be structured in any manner known to the art so drawings illustrating any of the articles within the scope of the invention need not be supplied for those skilled in the art to understand the nature of such articles or for their production.

DESCRIPTION OF THE PREFERRED EMBODIMENTS

A more complete understanding of the invention can be obtained by reference to preferred embodiments of the invention which are illustrated by the following specific examples of the new compostible sheets, articles and methods of the invention. It will be apparent to those skilled in the art that the examples involve use of some materials and reagents that are commercially available from known sources, e.g., chemical supply houses, so no details are given respecting them, although manufacturing sources may be indicated for assistance in replicating the compositions and articles.

In the examples, the percentages stated in [brackets] after each ingredient indicate the percentage by weight of the solids content of the composition created in the example. All parts are by weight.

EXAMPLE 1

A motor driven mixer is charged with 41.4 parts of natural rubber [67.5%] latex (62% solids), 31.8 parts of casein [12.5%] aqueous dispersion (15% solids) and 19.1 parts of carnauba wax [16.5%] slurry (33% solids). With the mixer operating at slow speed, 1.3 parts of titanium dioxide [3.4%] slurried in 6.4 parts of water are slowly added to the mixture which is then mixed for 20 minutes to produce a homogeneous, cream-like, aqueous dispersion.

EXAMPLE 2

A thin layer of the dispersion of Example 1 is cast on a release coated continuous belt using a conventional type draw bar and passed into a drying oven heated to about 120° C. Upon emerging from the oven, the resulting sheet of about 1-1.25 mil thickness is stripped from the belt and rolled up on a mandrel. When tested in accordance the ASTM standard test methods D-882-83 for tensile properties of thin plastic sheeting, one inch wide strips of the sheet are found to have, at an elongation of 450-500%, an ultimate tensile strength of 400-450 grams per inch of width and require a force of 275 grams to produce 100% elongation.

The sheet when tested for water permeability with a column of water six inches high imposed for 30 minutes against the top surface of the sheet fails to pass any water to the bottom surface of the sheet.

EXAMPLE 3

The procedure of Example 1 is repeated except that a 10% aqueous dispersion of 4 parts of yeast [9.7%] is charged into the blender with the rubber [61.0%], casein [11.3%], wax [15.0%] and $TiO_2$ [3.0%]. A cast sheet formed and tested as in Example 2 exhibited, after 5 days storage at ambient temperature, an ultimate tensile strength of 220-270 grams/in. width at an elongation of 600-700% and required a pull of 130-140 grams to produce an elongation of 100%.

EXAMPLE 4

A motor driven mixer is charged with 39.9 parts of natural rubber [61.3%] latex (62% solids), 30.7 parts of casein [11.4%] aqueous dispersion (15% solids) and 18.4 parts of carnauba wax [15.0%] slurry (33% solids). With the mixer operating at slow speed, 1.2 parts of titanium dioxide [3.0%] slurried in 6.4 parts of water and 9.8 part of polystyrene [9.2%] emulsion (37.8% solids) are slowly added to the mixture which is then mixed for 20 minutes to produce a homogeneous aqueous dispersion.

EXAMPLE 5

Using the procedure of Example 2, a sheet of about 1 mil thickness is cast from the aqueous dispersion of Example 4. Under test pursuant to ASTM 882-83, test strips of the sheet at a breaking elongation of 450-500% had a tensile strength of 750-950 grams and required a pull of 300-320 grams for a 100% elongation.

EXAMPLE 6

A specimen of the sheet prepared in Example 2 is placed in a compost bin on which a small amount of yeast dispersion had been sprayed and mixed with the compost. After three weeks of burial in the compost pile, it is found that the sheet is completely decomposed. Hence, no tensile tests are performed.

EXAMPLE 7

A motor driven mixer is charged with 7.9 parts of dry clay (Nytal 400 TM )[21.7%], 2.0 parts of titanium dioxide [4.3%] aqueous slurry (77% solids), and 13.8 parts water containing 0.1% surface active agent (Surfynol 440 TM ). With the mixer operating at slow speed, 15.8 parts of natural rubber [27.0%] latex (62% solids), 19.8 parts of carnauba wax [18.0%] slurry (33% solids), 24.9 parts of casein [10.2%] solution (15% solids) and 15.8 parts of resin modified styrene-isoprene-styrene copolymer [18.7] emulsion (43% solids) (Prinlin B7137X-1 TM ) are added and mixing is continued for 30 minutes to produce an cream-like aqueous dispersion.

Thin cast sheets formed as described in Example 2 exhibit properties comparable to those of Examples 2 and 5.

EXAMPLE 8

The procedures of Examples 1, 4 and 7 are repeated but with substitution of dextrose, starch or mixtures thereof for some or all of the casein. When cast sheets with thickness of about 1 to 2 mils of the resulting compositions are prepared and tested as in Example 2, they are all found to have a tensile strength of at least 200 grams per inch of width and to be water impermeable for at least 30 minutes against a six inch head of water.

EXAMPLE 9

Sheets prepared per Examples 2 and 5 were cut into rectangular sections of the required size to form outer covers 4 for disposable diapers 2 as disclosed in U.S. Pat. No. 4,769,024. In the resulting diapers, the back covers thereof were found to satisfactorily prevent urine absorbed in the absorbent mat 8 from penetrating through the back of the diapers during use on infants. When such diapers were buried in a compost pile, their outer covers mostly degraded in less than sixty days.

While natural rubber is a preferred elastomer for use in forming the moisture barrier sheets used in construction of articles of the invention, other C4-C6 alkadiene elastomers, including mixtures thereof, may be used. Examples include styrene-butadiene rubbers, acrylonitrile-butadiene rubbers, butadiene rubbers, acrylate-butadiene rubbers, and elastomeric styrene-butadiene, styrene-isoprene, styrene-isoprene-butadiene block copolymers and equivalent elastomers.

Casein is a preferred modifier for use in production of compostible sheets of the invention. However, this may be substituted, in whole or in part, by equivalent animal and plant proteins, e.g., soybean protein, dextrose, starch and mixtures thereof.

A variety of fillers may be used in formulation of the new compostible sheets, e.g., caulk, garnet, clays, fume silica, talc, lampblack, graphite, kaolin, magnesite, mica, quartz alumina, aluminum stearate, magnesia, barium sulfate, chrome oxide, cellulose fibers, nylon monofilament cuttings, and equivalent materials. Inorganic fillers are preferred.

A variety of natural and synthetic waxes, including mixtures thereof, may be used in production of the new compostible sheets, e.g., paraffin wax, beeswax, spermaceti, and equivalent materials, including hydrogenated fats or the like.

Styrene resins useable in accordance with the invention are those styrene homopolymers or copolymers that are resinous in nature rather than elastomeric, including polystyrene, resinous styrene-butadiene, styrene-isoprene, styrene-isoprene-butadiene block copolymers, styrene-alkyl acrylate copolymers, styrene-vinyl carboxylate copolymers and equivalent styrene resins.

In addition to the various components elucidated above, the compostible sheets of the invention may contain minor amounts, e.g., 0.1-10%, of various additives known in the art as useable in production of rubber-like sheets, e.g., processing aids such as bis-steramide and euricamide which improve slip. While additives can include anti-oxidants, stabilizers or the like, inclusion of such materials may be counterproductive in decreasing or destroying the compostibility of the new barrier sheets and articles. In this connection, inclusion of vulcanizers, curing agents and the like or bactericides or the like is to be avoided.

The embodiments of the invention in which an exclusive property or privilege is claimed are defined as follows:

1. A disposable article comprising a compostible flexible sheet composed of an unvulcanized, uncured homogeneous mixture of a major percentage of natural rubber with lesser percentages of a modifier selected from casein or equivalent animal or plant protein, dextrose, starch and mixtures thereof and inorganic filler, wherein said sheet has a thickness of about 1 to 10 mils and a tensile strength of at least 200 grams per inch of width.

2. A disposable article comprising as an independent component thereof a compostible flexible sheet composed of the following ingredients in the stated percentages by weight:

| unvulcanized, uncured C4-C6 alkadiene elastomer | 20-80%, |
|---|---|
| modifier selected from animal and plant protein, dextrose, starch or mixtures thereof | 5-20%, |
| inorganic filler | 1-40%, |
| wax | 0-30%, |
| styrene resin | 0-40%, |
| additive | 0-10% |
| yeast | 0-20%. |

3. The article of claim 2 which is a disposable diaper wherein said elastomer is natural rubber, said inorganic filler is selected from titanium dioxide and clay and said styrene resin is selected from polystyrene and styrene-/alkadiene copolymers.

4. The disposable diaper of claim 3 wherein said sheet consists essentially of the following ingredients in the stated percentages by weight:

| unvulcanized, uncured natural rubber | 65-75%, |
|---|---|
| casein | 10-15%, |
| wax | 10-20%, |
| inorganic filler | 5-20%. |

5. The diaper of claim 3 wherein said sheet has a thickness of about 1 to 2 mils and a tensile strength of at least 200 grams per inch of width.

6. The diaper of claim 3 wherein said sheet has a tensile strength of at least 400 grams per inch of width at an elongation of at least 400%.

7. A disposable garment comprising a compostible flexible sheet about 1 to 10 mils thick composed of a homogeneous mixture of the following ingredients in the stated percentages by weight:

| unvulcanized, uncured C4-C6 alkadiene elastomer | 50-80%, |
|---|---|
| modifier selected from animal and plant protein, dextrose, starch or mixtures thereof | 5-20%, |
| inorganic filler | 1-40%, |
| wax | 0-30%, |
| styrene resin | 0-40%, |
| additive | 0-10% |
| yeast | 0-20%. |

8. The disposable garment of claim 7 wherein said elastomer is natural rubber, said inorganic filler is selected from titanium dioxide and clay and said styrene resin is selected from polystyrene and styrene/alkadiene copolymers.

9. The disposable garment of claim 7 which is a diaper.

10. The disposable garment of claim 7 which is selected from surgical gowns, bibs and aprons.

11. The disposable garment of claim 7 wherein said sheet has a thickness of about 1 to 2 mils and a tensile strength of at least 200 grams per inch of width.

12. The disposable garment of claim 7 wherein said sheet consists essentially of the following ingredients in the stated percentages by weight:

| unvulcanized, uncured natural rubber | 45-75%, |
|---|---|
| casein | 10-15%, |
| wax | 10-20%, |
| inorganic filler | 5-20%. |

* * * * *